United States Patent [19]
Sharrock

[11] Patent Number: 5,916,179
[45] Date of Patent: Jun. 29, 1999

[54] SYSTEM AND METHOD FOR REDUCING IATROGENIC DAMAGE TO NERVES

[76] Inventor: Nigel Sharrock, 525 E. 86th St., Apt. 12F-G, New York, N.Y. 10028

[21] Appl. No.: 08/844,097

[22] Filed: Apr. 18, 1997

[51] Int. Cl.⁶ .................................................. A61B 5/05
[52] U.S. Cl. ......................... 600/587; 600/398; 600/553
[58] Field of Search ................................... 600/398, 407, 600/554, 587, 553; 128/897, 898

[56] References Cited

U.S. PATENT DOCUMENTS

| | | | |
|---|---|---|---|
| 3,757,770 | 9/1973 | Brayshaw et al. | 128/2 R |
| 3,911,903 | 10/1975 | Gee et al. | 128/2.05 Q |
| 3,958,558 | 5/1976 | Dunphy et al. | 128/2 P |
| 4,089,329 | 5/1978 | Couvillon | 128/2 T |
| 4,165,736 | 8/1979 | Wolfson | 128/687 |
| 4,281,662 | 8/1981 | Brent | 128/676 |
| 4,470,965 | 9/1984 | Wolf et al. | 424/80 |
| 4,519,401 | 5/1985 | Ko et al. | 118/748 |
| 4,548,205 | 10/1985 | Armeniades et al. | 128/748 |
| 4,629,424 | 12/1986 | Lauks et al. | 433/6 |
| 4,749,993 | 6/1988 | Szabo et al. | 340/870.31 |
| 4,825,873 | 5/1989 | Kohayakawa | 128/648 |
| 4,846,191 | 7/1989 | Brockway et al. | 128/748 |
| 4,958,645 | 9/1990 | Cadell et al. | 128/903 |
| 4,970,491 | 11/1990 | Saint et al. | 340/447 |
| 4,981,139 | 1/1991 | Pfohl | 128/671 |
| 5,032,020 | 7/1991 | Robert | 351/219 |
| 5,092,334 | 3/1992 | Nishio et al. | 128/648 |
| 5,107,853 | 4/1992 | Plyter | 128/744 |
| 5,114,070 | 5/1992 | Lilja et al. | 236/49.3 |
| 5,179,953 | 1/1993 | Kursar | 128/645 |
| 5,181,423 | 1/1993 | Philipps et al. | 73/724 |
| 5,181,522 | 1/1993 | McEwen | 128/748 |
| 5,183,044 | 2/1993 | Nishio et al. | 128/648 |
| 5,215,523 | 6/1993 | Williams et al. | 604/97 |
| 5,284,153 | 2/1994 | Raymond et al. | 128/741 |
| 5,284,154 | 2/1994 | Raymond et al. | 128/741 |
| 5,289,160 | 2/1994 | Fiorletta | 340/447 |
| 5,301,683 | 4/1994 | Durkan | 128/744 |
| 5,318,533 | 6/1994 | Adams et al. | 604/97 |
| 5,349,955 | 9/1994 | Suzuki | 128/645 |
| 5,382,924 | 1/1995 | Pardoen et al. | 332/100 |
| 5,387,194 | 2/1995 | Williams et al. | 604/97 |
| 5,389,118 | 2/1995 | Hinterman et al. | 51/295 |
| 5,396,888 | 3/1995 | Massie et al. | 128/649 |
| 5,408,731 | 4/1995 | Berggvist et al. | 29/25.41 |
| 5,415,167 | 5/1995 | Wilk | 128/653.1 |
| 5,417,717 | 5/1995 | Salo et al. | 607/18 |
| 5,439,552 | 8/1995 | Moret | 216/2 |
| 5,451,959 | 9/1995 | Schuermann | 342/51 |
| 5,453,091 | 9/1995 | Taylor et al. | 604/100 |
| 5,454,266 | 10/1995 | Chevroulet | D73/514.18 |
| 5,473,635 | 12/1995 | Chevroulet | 375/287 |
| 5,483,695 | 1/1996 | Pardoen | 455/314 |
| 5,483,826 | 1/1996 | Schultz et al. | 73/146.5 |
| 5,485,116 | 1/1996 | Cserveny et al. | 327/537 |
| 5,485,848 | 1/1996 | Jackson et al. | 128/672 |
| 5,488,869 | 2/1996 | Renaud | 73/724 |
| 5,508,636 | 4/1996 | Mange et al. | 326/38 |
| 5,523,808 | 6/1996 | Kohayakawa | 351/210 |
| 5,531,128 | 7/1996 | Ryhanen | 73/862.623 |
| 5,535,626 | 7/1996 | Bullis et al. | 73/514.32 |
| 5,541,600 | 7/1996 | Blumenkrantz | 341/139 |
| 5,546,070 | 8/1996 | Ellmann et al. | 340/442 |
| 5,562,621 | 10/1996 | Claude et al. | 604/100 |
| 5,579,149 | 11/1996 | Moret et al. | 359/223 |
| 5,587,580 | 12/1996 | Venier et al. | 250/206.1 |

*Primary Examiner*—Marvin M. Lateef
*Assistant Examiner*—Eleni Mantis Mercader
*Attorney, Agent, or Firm*—Milde, Hoffberg & Macklin, LLP

[57] ABSTRACT

A method for predicting peripheral nerve damage comprising the steps of placing a pressure transducer on the skin of a patient proximate to a peripheral nerve; measuring the pressure with the pressure transducer over time; and estimating a damage to the nerve based on the pressure and duration of application and a nerve damage model.

36 Claims, 5 Drawing Sheets

SYSTEM AND METHOD FOR REDUCING IATROGENIC DAMAGE TO NERVES

FIELD OF THE INVENTION

The present invention relates to the field of the prevention of iatrogenic injury to patients during procedures, and more particular to systems and methods for reducing iatrogenic peripheral neuropathy due to general anesthesia.

BACKGROUND OF THE INVENTION

Discovery of Peripheral nerve injuries are not uncommon following surgery, and nowadays constitute a major source of postoperative anesthetic-related malpractice claims and postoperative morbidity. This problem has been the subject of considerable interest in recent years, with a number of review articles being published. The exact cause is unclear, but may involve stretching of nerves or more commonly extrinsic pressure applied over a nerve in such a way that it is compressed, usually against a bone. Thus, for a period of hours, the nerve is subjected to mechanical stresses, and remains in this compromised state throughout surgery. If the duration of surgery is long and the extrinsic force high, the nerve may be irreversibly injured. Lesser degrees of injury may result in immediate loss of function with gradual return of nerve function over weeks or months.

It is not known what combination of extrinsic pressure and duration results in irreversible nerve injury. However, it is commonly understood that leaning on an elbow can rapidly make the little finger go numb (due to mechanical forces operating on the ulnar nerve), and that sitting cross-legged for a while can numb the leg and foot due to pressure on the sciatic nerve. When we are awake, we recognize these warning symptoms and shift the weight off of the nerve, thereby relieving the pressure so that permanent injury does not result. These anecdotal reports suggest that the extrinsic pressure necessary to injure nerves may be regularly found in common situations, and may be due to the patient's own weight. Further, these reports also suggest that the forces necessary are not trivial, i.e., numbness does not normally occur without an identified provocation.

There are a number of sites where nerves may be compressed leading to postoperative neuropathy:

1. Ulnar nerve beneath the medial epicondyle (posterior inner aspect of the elbow). Extrinsic pressure here can compress the ulnar nerve against the medial epicondyle and/or olecranon.
2. Radial nerve over the posterior aspect of the arm midway between the shoulder and the elbow. The radial nerve here can be compressed against the humerus.
3. Peroneal nerve can be compressed as it passes around the fibula several inches below the outside of the knee.
4. The sciatic nerve can be compressed in the buttock as it passes between the ischium and the trochanter.
5. The femoral nerve in the groin can be compressed as it exits beneath the ilioinguinal ligament to enter the thigh. It can be compressed against the pubic ramus.
6. Lateral femoral cutaneous nerve of the thigh can be compressed by pressure against the anterior iliac spine.

Therefore, it is understood that external forces can damage nerves, however, suitable methods and systems for determining when such forces are sufficient to cause damage are not readily available.

SUMMARY OF THE INVENTION

The present invention therefore provides a system for estimating potential injury to peripheral nerves by measuring a mechanical effect, e.g., a force, pressure or strain, applied over the nerve with a transducer proximate to the skin. These transducers are preferably situated near areas at risk for a particular operation, such as:

1. beneath the elbow if patients are lying on their back,
2. under the midpoint of the arm if additional pressure is applied there,
3. over the sciatic nerve in the buttocks if patients are in the sitting position,
4. over the femoral nerves or lateral femoral cutaneous nerves for patients in the prone position,
5. The sensationless skin of spinal cord injury patients.

There are a number of other applications for the present technology, including on the sole of the feet, particularly in the case of patients with bunions, incapacitated patients who may be bedridden and thus subject to pressure sores, or surgical patients who may be subject to damage to the eye and to nerves which are near the surface of the skin in the extremities. Of particular interest is the monitoring of ulnar nerve function in patients lying supine with their arms supinated and adducted, or else tucked in at their sides.

Transducers may also be applied to mechanical elements within the environment at high risk of applying pressure top the patient for extended periods. For example, surgical retractors, bed rails, and the like, may come into patient contact and thus compress nerves or cause ischemic injury.

Typically, two different types of transducers are employed. First, a bladder transducer includes a liquid or gas medium in a contained system, with an unshielded portion proximate to the area to be sensed, and a shielded portion leading to an electromechanical pressure transducer. The medium in the closed system may be, for example, water or glycerin. In this case, the bladder should be large enough to cover the area of potential injury, while small enough that localized pressure application may be reliably sensed. For example, the bladder for limb application is disk shaped, having a diameter between about 1–4 cm and between about 0.2–1 cm thick. The bladder is linked by semirigid hose to a pressure transducer, with a range of about 0–1000 mm Hg, and an accuracy of ±5%, and a sensitivity of 5 mm Hg. For example, companies such as Baxter mass produce suitable pressure transducers, which can be applied to a Band-Aid-type of adhesive patch quite simply.

Such a bladder will average an applied force over the area of the bladder, resulting in a pressure measurement. Generally, this averaging does not cause problems because (a) the force is physically averaged by the bladder, over the area measured by the bladder, and thus represents the actual pressure applied, and (b) the bladder covers the area of interest, and therefore the fact that the force may produce different pressures elsewhere is of little consequence.

Another suitable transducer is provided as a flat strip electro-mechanical transducer which is provided in close proximity to the skin. This transducer is designed to measure applied force, pressure or strain, and may include multiple segments, especially for large areas. These transducers may also be sensitive to other effects, which may correlate with nerve damage. A multielement transducer also allows signal processing to reduce noise by compensating for a common mode. These transducers may be applied to the skin as strips, e.g., on a self-adhesive backer, which is applied to the skin in a desired location. Because of the close patient contact, these transducers are preferably disposable. Further, these strip transducers need not be particularly accurate or linear in response, so long as they respond to pressures above about 50 mm Hg.

With bladder-type pressure transducers, the pressure applied to those areas can then be monitored by displaying or recording the pressure on a standard anesthetic monitor or on a special purpose device. The transducer is preferably disposable and may require calibration (i.e. zeroing) prior to use. If excessive pressure is detected, an alarm is sounded or the patient's position will automatically be altered. The system may also compute time-pressure products or other functions of time and pressure and issue warnings accordingly.

With strip transducers, a more specialized output device is provided, which either translates the reading into an applied force, pressure or strain, or directly computes a potential damage function and indicates an alarm if the probability of damage or damaging effect is high.

According to the present invention, known pressure transducers and pressure transducer systems may be employed. In order to minimize the number of transducers and the area of measurement of the transducer, it is preferable that the transducer be placed at or sensitive at the location of maximum force or maximum effect on the nerve. Often these places will coincide, but where they do not, two transducers or a multi-point transducer may be employed. For example, where a nerve passes in front of a bone, the point of crossing is generally the relevant position. The transducer may be affixed to the skin for example by a removable adhesive such as the type used in bandages and electrocardiagraphic transducers.

It should be noted that damage thresholds may vary with tissue temperature, blood pressure and pressure waveform, blood oxygenation, and other factors. Therefore, where ischemic injury is a major factor, the use of a pulse oximeter to measure the effect of an applied pressure on blood flow may be desired. The eye is particularly appropriate for optical measurements of blood oxygenation since it is optically accessible. On the other hand, where blood flow to the nerve does not correlate well to skin perfusion, or where mechanical injury predominates, the pulse oximetry technique will have less value.

In order to estimate ischemic damage to the tissues of the patient, the present invention may also incorporate a pulse oximeter system, in order to measure blood flow, which may also relate to the applied pressure, and further will provide information as to this profusion status of the underlying tissue. Typically, pulse oximeters employ a differential optical sensing element, sensitive to differences between hemoglobin and deoxyhemoglobin, using a red LED and an infrared LED, with a single photo detector. Other types of optical detection may also be used. In the present case, a baseline reading is obtained during application of the sensor. Thereafter, the sensor output may be used to determine oxygenation ratio of hemoglobin, or even the amount of hemoglobin within the optical field of view. This system may be applied to the skin, where it is presumed that capillary blood flow to the skin correlates with capillary blood flow in tissues under the skin subjected to the same forces, i.e., the nerve.

According to another embodiment of the present invention, a pressure sensor is affixed to the eyelid of a patient during surgical procedures. Since the orbit is a closed, semiliquid environment, the pressure on the surface of the eye near the eyelid will correspond to the pressure on the optic nerve. This pressure sensor detects externally applied pressure to the eye, which is a risk when a patient is unconscious or subject to general anesthesia.

The clinical setting in which blindness is apt to occur is where the patient is positioned in the prone position, with the eyes being compressed by an external force. When the blood pressure is lowered, as may occur during anesthesia, insufficient blood flow to the eye occurs. Thus, the ocular perfusion pressure is proportional to the blood pressure minus the external pressure, which may be measured by the transducer.

Therefore, an externally applied pressure can lead to injury to the eye or blindness. Therefore, by applying a pressure transducer on the eyelid, the intraocular pressure may be estimated, and if this pressure exceeds a "safe" pressure for in excess of a critical period, an alarm may be sounded so that the anesthesiologist may take corrective action. Thus, in the case of the eye, the damage is primarily ischemic damage due to reduced perfusion pressure. In this case, the threshold for damage may be simply determined by estimating blood flow optically to the retina under various applied pressures to the orbit. The pressure at which blood flow begins to be substantially compromised is the pressure at which damage is likely to occur. In practice, a safe threshold for an alarm condition will be set well below a hazardous level, which may be adjusted if too many false positive or distracting alarm conditions occur.

It is noted that other types of intraocular pressure sensing or estimating systems are known, and that these may be used in accordance with the present invention. For example, a known glaucoma screening system measures orbit indentation based on a stream of air.

Blood perfusion to the eye may also be estimated using optical sensors. One type of optical sensor is a pulse oximeter, which measured a state of blood oxygenation based on differential optical absorption of hemoglobin and deoxyhemoglobin. Such optical sensing may be applied through the lens of the eye to the retina. In this manner, retinal hypoxia may be directly measured.

Yet another method of determining retinal hypoxia or ischemia is based on the neural response to optical illumination of the retina. In this case, a light flashes on the retina, such as an light emitting diode (LED), incandescent bulb, electroluminescent element, or fiber optic element. Immediately after the illumination, the neural impulse generated in the retina, optic nerve and/or thalamus is measured. As this response is delayed or diminishes, it may presumed that retinal functioning is impaired. The sensor for detecting the retinal excitation is an electroencephalographic detector, which may be applied to the scalp. However, advantageously, a sensitive electrode may be applied near or on the eye, to more directly measure retinal excitation immediately after illumination. To measure both eyes, the illumination may alternate. Preferably, the electrodes are well shielded from other electrical systems in the operating room and suppress interference from other devices, such as electrosurgical devices.

In addition to the above-described transducer systems, the transducer may also be of any other known type.

In a preferred embodiment, some or all of the transducers or electrodes operate telemetrically, avoiding the need for many wires or cables, which themselves may result in skin trauma. For example, a telemetric pressure transducer system is disclosed in Allen, Roger, "Wireless Transceiver With Micromachined Sensor Detects Both Tire pressure and Temperature", Electronic Design, Nov. 16, 1996, p. 40, expressly incorporated herein by reference. Generally, temperature information is not required, and the pressure range of interest is in the 0 to 300 mm Hg range, rather than an expected range of tire pressures.

It is believed that peripheral nerves have a low probability of damage with pressures below about 50 mm Hg (e.g., pressures approaching cardiac diastolic pressure), which increases as a function of both time and pressure, above this pressure, up to systolic pressure. Above systolic pressure, it is likely that ischemic damage will occur, in addition to any mechanical damage due to the pressure, and therefore the time until irreversible damage begins will be in the order of tens of minutes. It is believed that the mechanical damage effects are characteristically different than ischemic effects, and that these may be modeled separately. These models may both estimate a degree of damage to the nerve at any point in time, or predict a future damage to the nerve should conditions remain the same or change at a constant rate.

The mechanism of pressure necrosis generally involves an externally applied pressure which exceeds the arterial or arteriolar profusion pressure, therefore blocking oxygenated blood flow to the tissue. This results in ischemic injury which may damage or kill nerve cells. As stated above, the mechanism of direct pressure damage is much speculated, and the particular parameters which correlate with neuropathy or neuropraxia are not fully defined. The parameters used by the present system may, however, be derived from anecdotal reports, animal studies, expert opinions, or other sources.

In general, the external applied pressure to cause these detrimental effects on otherwise healthy tissues is in excess of 75 mm Hg for over 10 minutes; and in most instances, the pressures are higher and the duration are longer. The actual pressures and times may vary for different patients and locations, and may especially vary where the tissue is not healthy, the patient has impaired circulation, or where nerve damage is preexisting.

A prediction takes the form of a time-damage relationship, which alerts the anesthesiologist before significant damage has occurred that the patient must be repositioned. The system may also include automatic repositioners or actuators, which act to relieve undue forces in advance of morbidity.

Ulnar nerve injury is the most common neuropraxia, and this is probably due to extrinsic pressure during procedures. In this case, information on actual trauma to the nerve may be obtained by measuring nerve conduction, or spontaneous nerve irritability, which may be detected at the hand through skin electrodes or needle electrodes.

Therefore, one preferred embodiment of the present invention includes a pressure transducer located on the skin of the forearm, near the elbow over the ulnar nerve. The pressure transducer is preferably either a disposable pressure transducer or a reusable pressure transducer with a hydraulic extension and a bulb which is placed over the site to be measured. An electronic monitor determines the pressure and calculates to predict the net effect of the applied pressure on the underlying tissue. Therefore, the electronic monitor includes generally safe thresholds or a model of tissue damage with respect to applied pressure, in order to alert the patient or care givers that damage may occur or be occurring. This model may be derived, for example, by expert analysis and review of reports of morbidity under specific circumstances. The model should, of course, have a margin of safety, especially where immobilization of the affected body portion is not critical to a medical procedure. This model may analyze, for example, the anatomical location, the patient's blood pressure, the presence of other conditions (e.g., diabetes), the patient's blood gas analysis, and of course, time and applied pressure. For example, in certain instances, nerves may be hypersensitive to mechanical factors. For example, in carpal tunnel syndrome, the ulnar nerve is quite sensitive to injury and applied pressure. In this case, the model accounts for this increased susceptibility, and for example, an alarm threshold may be reduced.

In a preferred embodiment, the electronic monitor may be separated from the patient and use for example, telemetry. The pressure transducer may operate as a modulated backscatter device, such as an addressable RF-ID tag or the like. See, e.g., Tuttle, John R., "Integrated Circuit Simplified Design of RFID Systems", *Microwaves and RF*, October 1996, pp. 103–109, incorporated herein by reference; Allan, Roger, "Wireless transceiver With micromachined Sensor Detects Both Tire Pressure and Temperature"; *Electronic Design,* Dec. 16, 1996, p 40, incorporated herein by reference.

In general the result of any alarm condition will of course be to alert the patient or the care giver to relieve the pressure on the nerve, the success of which may be determined by the same system, e.g. the transducer. It is noted that, while the external mechanical effect measured may be a force, pressure, strain, or the like, generally these are translated into macroscopic pressures to which the nerve is subjected by the surrounding tissues.

The electronic monitor may also be integrated with an automated actuator system which relieves pressure against the skin. For example a smart surface may control pressure against the body of a person. Such smart surfaces are available from BCAM (Biomechanics Corporation of America, Long Island, N.Y.). Further, a surface may be provided with a plurality of mechanical actuators which cyclically vary pressure on the skin in order to ensure adequate profusion toward block prolonged pressure against all underlying tissues, with the transducer provided to ensure pressure relief is effective.

The present invention thus relates to a system having a transducer placed externally, e.g., over the skin in proximity to a peripheral nerve, for the purpose of measuring or estimating a mechanical effect, which provides information about the macroscopic pressures which are applied to the nerve, allowing a prediction or estimation of damage that may occur or have occurred to the nerve, such as due to mechanical damage or pressure necrosis.

It is therefore an object according to the present invention to provide a method and system for predicting or estimating nerve damage due to external mechanical effects, comprising the steps of placing a transducer external to a patient at a location where a mechanical effect is sensed by the transducer correlates with a local pressure to which a nerve is subjected; measuring the mechanical effect over time by means of the transducer; and predicting and/or estimating a damage to the nerve based on the measured mechanical effect over time.

The prediction and/or estimate may be based on a model of nerve damage based on time-weighted pressure, a determination of ischemic damage to the nerve, and/or a nonischemic damage to the nerve.

In response to the prediction or estimate of damage, the system may produce an alarm, or automatically address the problem by controlling an actuator to relieve the pressure.

In predicting or estimating damage to the nerve, the characteristics of the patient may be taken into account, and an automated monitor may be adaptive to a clinical condition of the patient.

According to one object of the invention, a transducer is applied proximate to the skin proximate to the ulnar nerve. This transducer may include a fluid-filled bladder in proximity to the skin, a planar electromechanical transducer affixed to the skin having one or more regions, each region producing an output. In the case of multiple inputs representing a single nerve, the various outputs may be processed or combined to yield a single parameter, for example, an output representing the largest applied force.

According to another object of the invention, a transducer is applied in proximity to the eye. This transducer may include a fluid filled bladder placed adjacent to the eyelid, an optical sensor, or a pneumatic sensor.

It is a still further object of the invention to provide a system and method for predicting neuropraxic effects, comprising the steps of directing optical sensor, differentially sensitive to hemoglobin in an oxygenated and deoxygenated state, toward vital tissues having a pressure which corresponds to a pressure to which a nerve is subjected; estimating a blood perfusion to the nerve over time based on the optical sensor; and predicting a damage to the nerve based on the estimate of blood perfusion over time and a modeled sensitivity of the nerve to ischemic injury. The optical sensor may, for example, sense capillary blood in skin or retinal blood flow.

It is a still further object of the invention to estimate a pressure applied to the nerve over time and predicting a damage to the nerve based on the estimate of pressure applied to the nerve over time and a modeled sensitivity of the nerve to mechanical injury.

The pressure may also be measured in a variety of other ways, including miicromachined silicon pressure sensors, capacitive sensors, or other known plethysmography techniques. Further, the pressure data may be transmitted though wires or cables, fiber optics, or wirelessly, as an acoustic, optical, electromagnetic or radio frequency signal. See, U.S. Pat. Nos.: 5,488,869, 5,531,626, 5,531,128, 5,436,695, 5,473,636, 5,454,266, 5,439,552, 5,408,731, 5,382,924, 5,215,523, 5,562,621, 5,453,091, 5,318,533, 5,387,194, 4,749,993, 5,485,848, 5,289,160, 4,970,491, 3,958,558, 5,546,070, 5,483,826, 5,181,423, 4,629,424, 4,519,401, 4,958,645, 5,451,959, 5,417,717, 4,981,139, 4,846,191, 3,757,770, 5,396,888, 4,281,662, 5,349,955, 5,183,044, 5,032,020, 5,523,808, 5,092,334, 4,825,873, 4,548,205, 3,911,903, 5,179,953, and 4,165,736, each of which is incorporated herein in its entirety. U.S. Pat. No. 5,179,953 discloses an ocular pressure sensing "contact lens", with a memory. According to the present invention, for example, the measurements are not stored, but rather transmitted telemetrically to a control unit which monitors the ocular pressure in real time and determines the existence of alarm conditions.

It is another object of the invention to provide a sensor for predicting retinal damage due to applied forces, comprising a fluid filled bulb adapted for placement proximate to the eyelid, covering the orbit and a tube for transmitting a pressure of the fluid to a pressure transducer. A pressure transducer may be provided for measuring a pressure of the fluid and an analyzer for determining risk of damage to the retina based on applied forces over time.

BRIEF DESCRIPTION OF THE DRAWINGS

The preferred embodiments of the invention will now be described with respect to the drawings, in which.

DETAILED DESCRIPTION OF THE PREFERRED EMBODIMENTS

Figure 1:
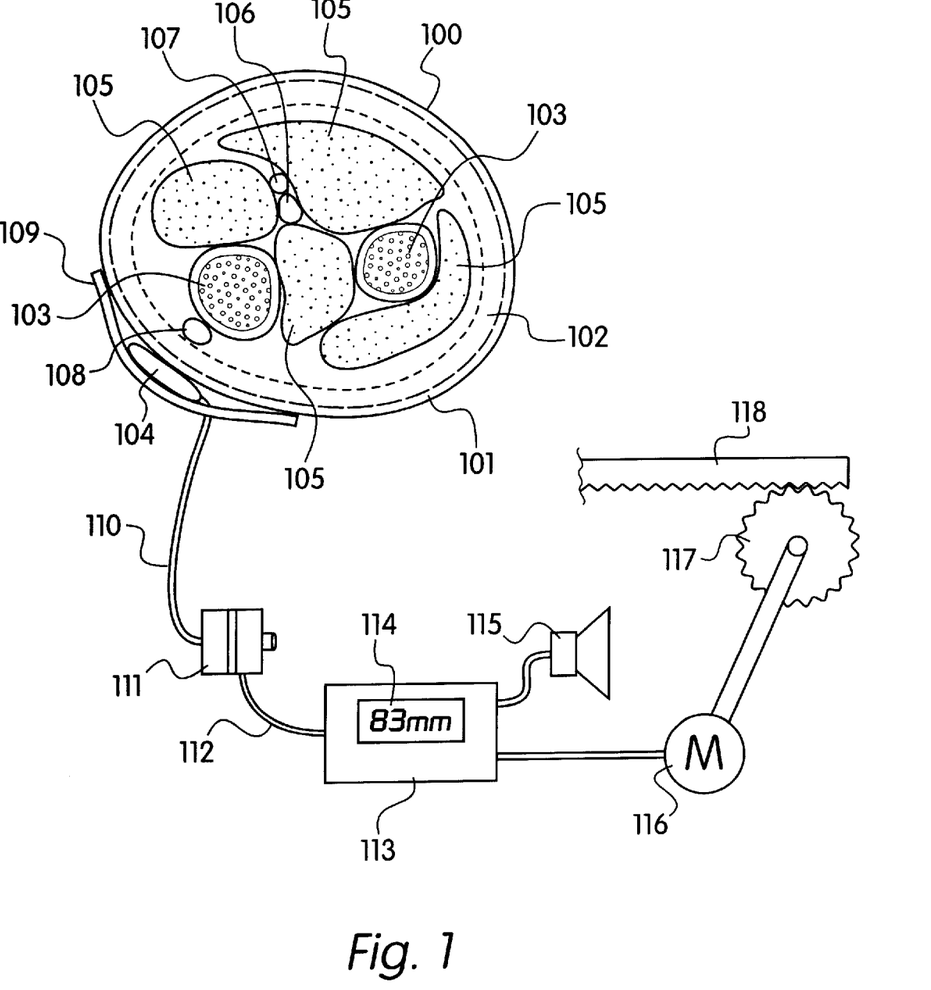
FIG. 1 shows a cross section of a limb, showing a bone, nerve, muscle, skin and a bulb pressure transducer system according to the present invention, adhered to the skin.

FIG. 1 shows, in cross section, a nerve passing over a bone, for example in the forearm. A force applied to the skin over the nerve compresses the nerve against the bone, causing a mechanical injury and ischemia. The pressure transducer measures a force on the skin, which corresponds to the force on the nerve.

In typical surgical procedures, there may be little choice but to have the patient's limbs support at least their own weight, and often to support additional weight of the torso. Further, the nerves at issue, except possibly the ulnar nerve, generally are believed to have a moderate resistance to pressure injury. Thus, the alarm thresholds may be set relatively high, e.g., in excess of systolic pressure less 10–20 mm Hg for greater than five minutes. This compromise is necessary in order to avoid unnecessarily disturbing a surgeon during a procedure. On the other hand, where danger of nerve damage is imminent, this may be addressed by alerting the anesthesiologist or automatically relieving the force.

As shown in FIG. 1, a cross section of a forearm 100 shows an outer layer of skin 101, which overlies subcutaneous tissue 102, having varying thickness. Bones 103, support the forearm 100. The cross section also shows various muscles 105, and blood vessels 106, 107. The nerve 108, in this case the ulnar nerve, overlies the bone 103, in this case the ulna, and is relatively unprotected by other tissues. Thus, it is particularly subject to external mechanical effects. A transducer, including a bladder 104, is connected by a hose 110 to an electromechanical pressure transducer 111. The bladder is adhered to the skin with an adhesive strip 109. The electromechanical pressure transducer 111, in turn, is connected to a monitor 113, hailing a visual display 114 of the pressure, an audio alert 115, an optionally, a control for an actuator 116, which acts, for example, as a servo to drive a mechanical system 117, 118, and relieve the pressure on the nerve 108.

Figure 2:
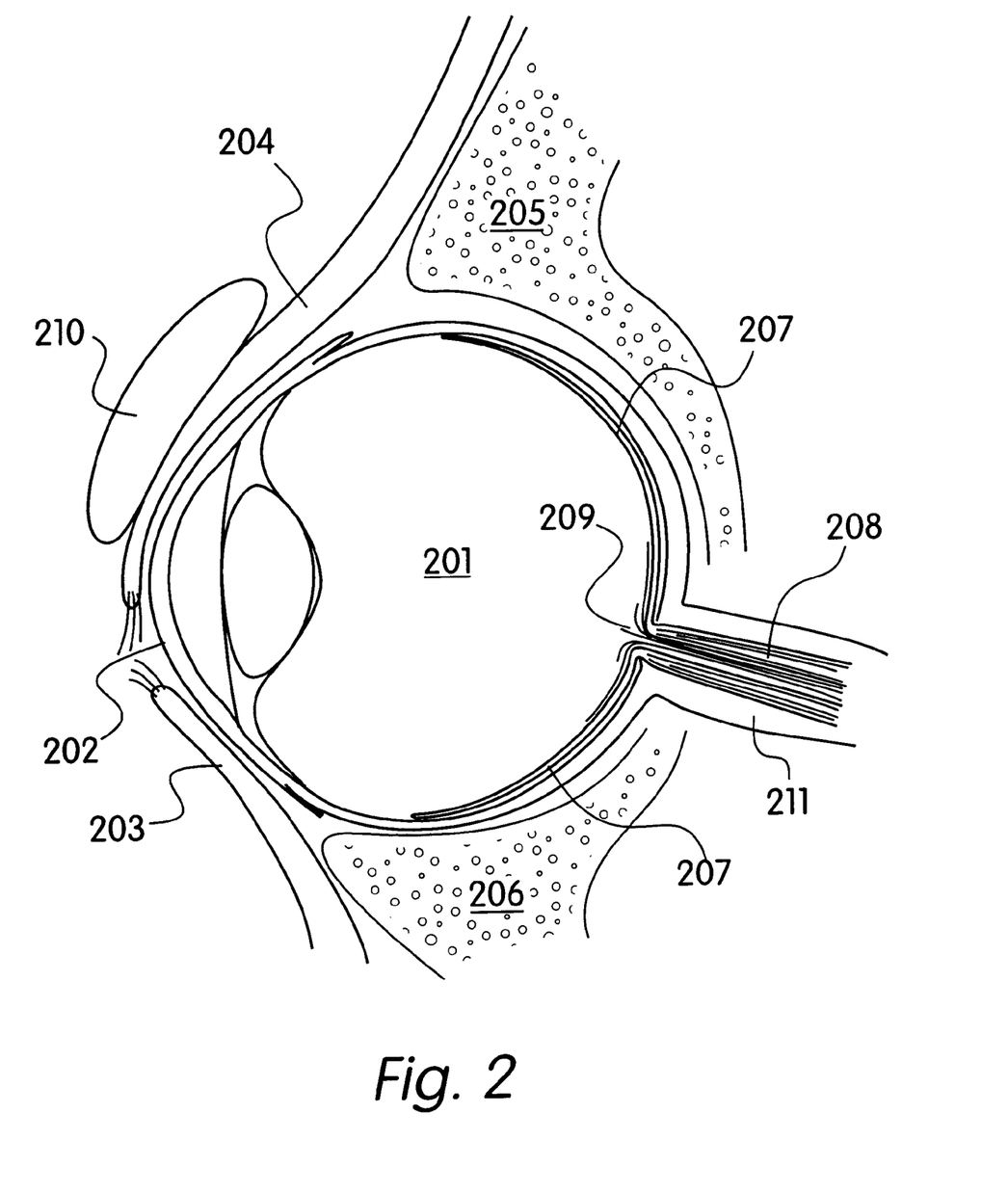
FIG. 2 is a perspective view of a pressure transducer applied proximate to the orbit to estimate intraocular pressure.

FIG. 2 shows an intraocular pressure monitor. This monitor covers the eye, and thus any external pressure applied to the eye must pass through the sensor system. Any pressure in excess of diastolic pressure will tend to impair blood flow to the eye and thus cause an alarm state. This monitor is particularly useful during procedures performed in the prone position, wherein blindness is most likely to occur with a combination of external pressure and low blood pressure. It is noted that, during a procedure, no external pressure generally need be applied to the eye, and, other than maxillofacial surgery, the eye is often readily accessible to the anesthesiologist without substantially disturbing the surgeon. Therefore, the sensor may be designed to generate an alarm condition, for example, if the applied pressure exceeds the diastolic pressure for more than ten seconds continuous, and/or greater than diastolic pressure for more than 20% over a five minute interval, and/or an average applied pressure of greater than diastolic pressure over a five minute interval. Predetermined thresholds may also be applied, in addition to the adaptive thresholds based on blood pressure or other factors.

In FIG. 2, the eye 201 is surrounded by a bony socket 205, 206 forming the orbit, with a rear aperture, through which the optic nerve 211 and retinal artery enter the eye 201. The retinal artery 208 has branches 209, which supply blood the retina 207. A bladder 210, overlies the upper eyelid 204, which is closed during a procedure. The lower eyelid 203 may also be covered. The bladder 210 leads to a monitor similar to that shown in FIG 1.

Figure 3:
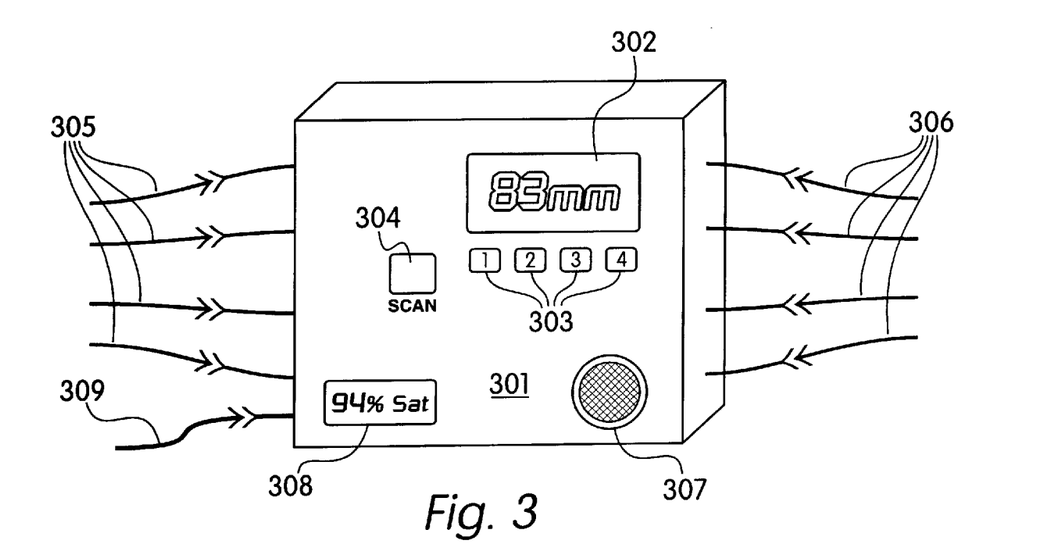
FIG. 3 is a block diagram of a monitor according to the present invention.

FIG. 3 shows a monitor according to the present invention. The pressure monitor includes one or more pressure inputs, for example fluid-filled tubes or electronic inputs. The fluid filled tubes interface with pressure transducers, which produce electrical signals. The electrical signals are analyzed by a computerized monitor, which provides a simple threshold for alarm, a time and pressure threshold for alarm, and a more complex model for damage to the nerve. The alarm is, for example, an audio, visual, or tactile alert to the anesthesiologist.

The monitor 301 shown in FIG. 3 provides four pressure transducer inputs 305, which are processed to produce an estimated pressure, which is displayed. Control switches 303, 304, allow the user to select a particular transducer 303, or to scan all the channels 304. The monitor 301 also includes a pulse oximeter 308 with a display, and a separate input. This pulse oximeter may be used to determine various general physiological conditions of the patient to set thresholds, or to determine site-specific ischemia. In the later case, the pulse oximetry input would be of reduced value with respect to other anatomical locations.

Figure 4:
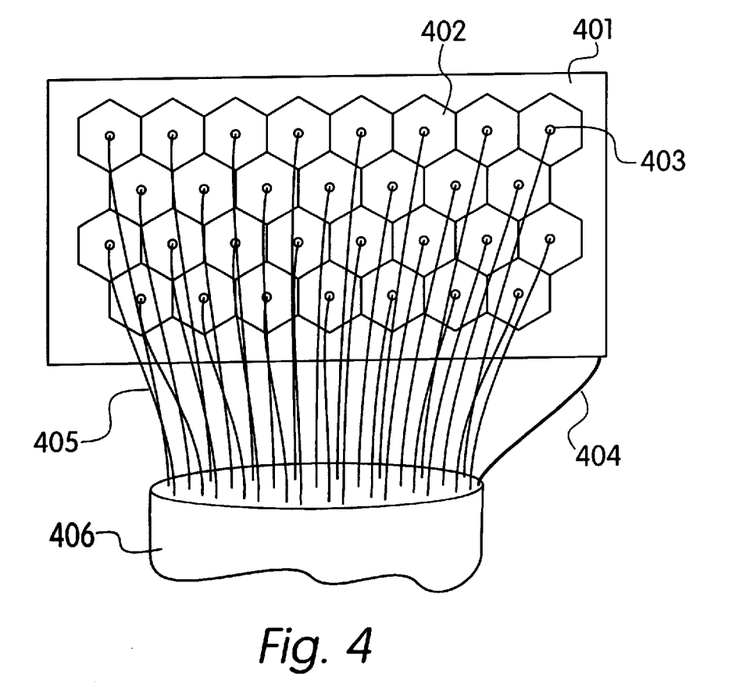
FIG. 4 is a top view of a segmented transducer according to the present invention.

An electronic strip pressure transducer is shown in FIG. 4. This transducer estimates the pressure based on a force applied to the transducer itself. A multisegmented transducer allows relatively imprecise placement of the transducer patch, with alarms based on the maximum pressures detected, or a subsequent determination of the location of the nerve, for example by a nerve conduction study.

The strip transducer is provided as a sheet 401 with a self-adhesive backing. The sheet is conductive, and provides a common ground 404 for the sensing elements. The sensing elements form a regular array, for example of hexagonal elements 402, each sensitive to an applied force normal to the surface of the sheet 401. Each element 402 is connected at a connection point 403 by a separate conductor 405 to a monitor (not shown), through a cable 406.

Figure 5:
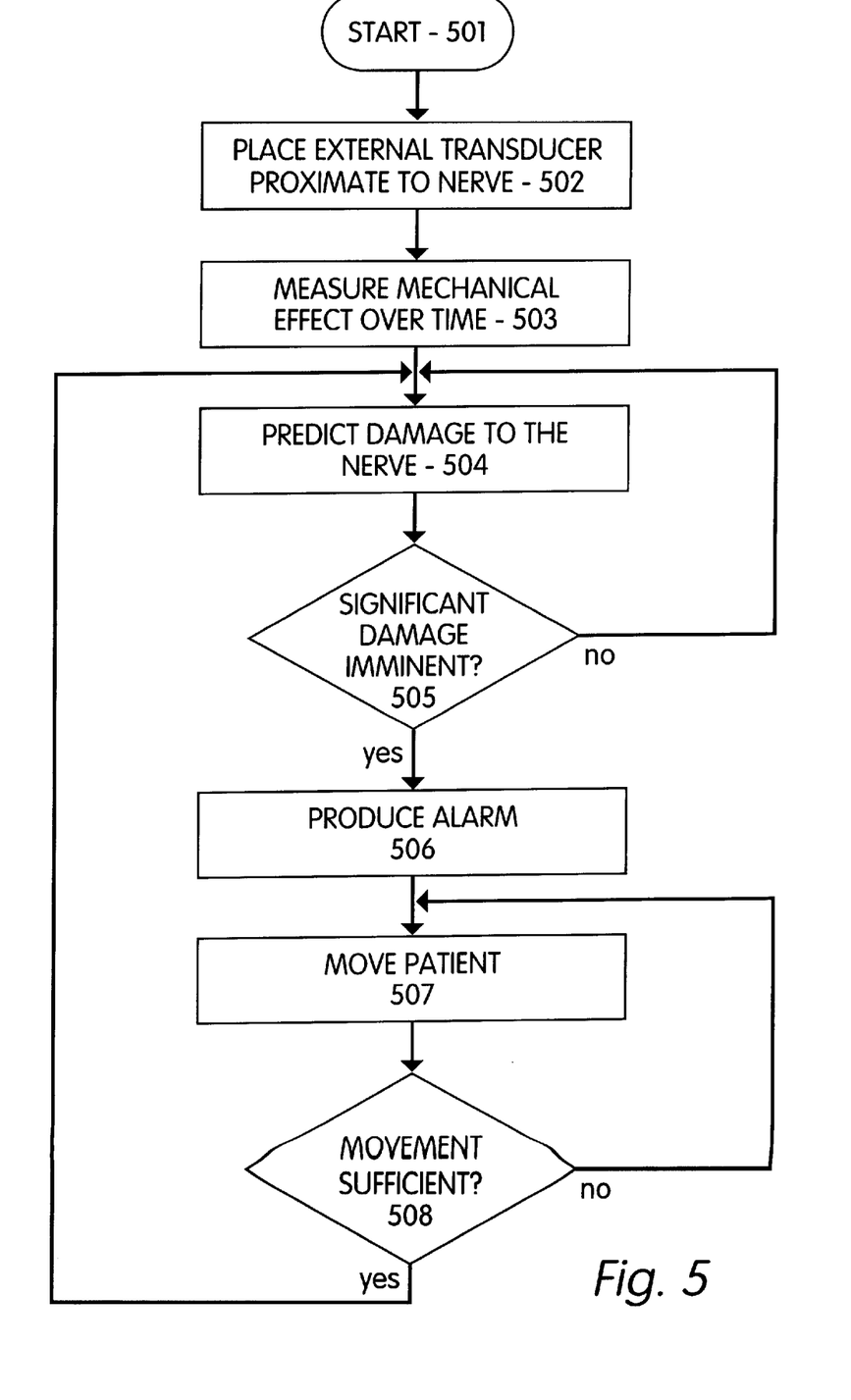
FIG. 5 is a flowchart showing the sequence of a method according to the present invention.

FIG. 5 shows a method for operating a pressure monitor according to the present invention. The anesthesiologist places a transducer proximate to a nerve of interest. The During the procedure, the patient is anesthetized and immobilized. The pressure is monitored, and compared against one or more patterns of likely injury. Thus, if the pressure at any time exceeds a peak pressure, for example 350 mm Hg, an alarm is sounded. Using a simple model, if the pressure time product exceeds a threshold, an alarm is also sounded. For example, a pressure product in excess or (systolic pressure -20*5) mm Hg×minutes, with a rolling average over 8 minutes, might be a typical threshold. Finally, a more subtle model may be provided which includes much more information about the patient's susceptibility to neuropathy may be provided as the basis for the alarm, possibly integrating minutes or hours of data. If any alarm condition exists, the anesthesiologist is alerted to take corrective action. In general, transients may be suppressed as being noise or of little relevance, in favor or prolonged measurements.

As shown in FIG. 5, at the start 501, an external transducer is placed proximate to a nerve 502. The transducer output is then used to measure a mechanical effect over time 503. A control system predicts damage to the nerve 504, either at present or into the future under comparable conditions. Where significant damage is occurring or is imminent 505, an alarm is produced 506. The patient (or object in contact with the patient) is moved 507, to relieve the force causing the pressure on the patient. The movement may be automated or manual. A closed loop control may be implemented, using the transducer to determine whether the executed movement was sufficient 508. If not, the patient may again be moved 507, until the force is alleviated.

Figure 6:
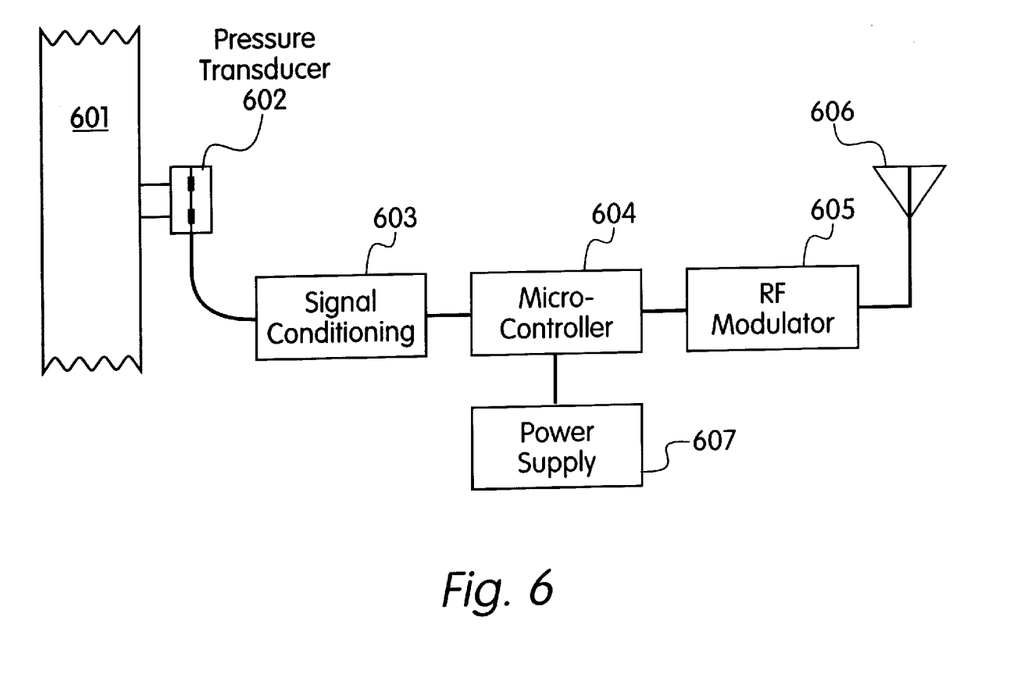
FIG. 6 is a schematic diagram of a telemetric pressure sensor.

FIG. 6 shows a telemetric pressure sensing system. A compliant closed bladder 601, containing a gas or liquid, is provided in contact with the area to be measured, providing a spatial averaging of the applied pressure over the area of the bladder. The gas or liquid is in communication with a pressure transducer 602, which is, for example, a piezoresistive silicon sensor. A signal conditioning module 603, which is, for example, a micropower operational amplifier, conditions the signal and filters noise. A microcontroller 604, having analog to digital conversion capabilities, receives the conditioned signals and generates an encoded data stream, which, for example, includes redundancy as well as error detection and/or correction codes. The encoded stream is fed to a radio frequency modulator 605, which, in turn, feeds an antenna 606. The microcontroller 604 controls a power supply 607, in order to limit power dissipation. The power supply 607 may include, for example, a lithium button cell. The operation of the system may be modulated, for example, to transmit data once per second or once per 10 seconds. In the later case, especially, the transmission preferably includes data relating to a plurality of pressure measurements.

There has thus been shown and described a novel system and method which fulfills all the objects and advantages sought therefor. Many changes, modifications, variations and other uses and applications of the subject invention, will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is limited only by the claims which follow.

What is claimed is:

1. A method for predicting nerve damage due to external mechanical effects, comprising the steps of:

(a) placing a transducer external to a patient at a location where a mechanical effect is sensed by the transducer correlates with a local pressure to which a nerve is subjected;

(b) measuring the mechanical effect over time by means of the transducer; and (c) predicting a damage to the nerve based on the measured mechanical effect over time, and a model of susceptibility of the nerve to damage.

2. The method according to claim 1, wherein said prediction is based on a model of nerve damage based on time-weighted pressure.

3. The method according to claim 1, wherein said prediction comprises an estimate based on an estimate of ischemic damage to the nerve.

4. The method according to claim 1, wherein said prediction comprises an estimate of non-ischemic damage to the nerve.

5. The method according to claim 1, further comprising the step of producing an alarm if the estimate of damage exceeds a threshold.

6. The method according to claim 5, wherein said threshold is adaptive to a clinical condition of the patient.

7. The method according to claim 1, further comprising the step of relieving pressure on the nerve.

8. The method according to claim 7, wherein the pressure on the nerve is relieved automatically.

9. The method according to claim 8, further comprising the step of controlling an actuator to relieve a pressure on the nerve.

10. The method according to claim 1, further comprising the step of estimating a damage to the nerve.

11. The method according to claim 10, further comprising the step of producing alarms if either the prediction or estimate exceed respective thresholds.

12. The method according to claim 1, wherein said transducer is applied proximate to the skin proximate to the ulnar nerve.

13. The method according to claim 1, wherein the transducer comprises a fluid-filled bladder in proximity to the skin.

14. The method according to claim 1, wherein the transducer comprises a planar electromechanical transducer affixed to the skin.

15. The method according to claim 14, wherein the transducer comprises a plurality of regions, each region producing an output.

16. The method according to claim 15, further comprising the step of basing said prediction on an output representing the largest applied force.

17. The method according to claim 1, wherein the transducer is applied in proximity to the eye.

18. The method according to claim 17, wherein the transducer comprises a fluid filled bladder placed adjacent to the eyelid.

19. The method according to claim 1, further comprising the step of wirelessly transmitting a signal corresponding to the mechanical effect.

20. The method according to claim 1, further comprising the step of adapting the model of susceptibility of the nerve to damage based on a clinical state of the patient.

21. A method for predicting nerve damage due to external mechanical effects, comprising the steps of:
   (a) placing a transducer external to a patient at a location where an external mechanical effect is sensed by the transducer correlates with a local pressure to which a nerve is subjected;
   (b) measuring the external mechanical effect over time by means of the transducer; and
   (c) predicting a damage to the nerve based on the magnitude and duration of the measured external mechanical effect.

22. A method for predicting neuropraxic effects, comprising the steps of:
   (a) directing an optical sensor, differentially sensitive to hemoglobin in an oxygenated and deoxygenated state, toward vital tissues having a pressure which corresponds to a pressure to which a nerve is subjected;
   (b) estimating a blood perfusion to the nerve over time based on the optical sensor; and
   (c) predicting a damage to the nerve based on the estimate of blood perfusion over time and a modeled sensitivity of the nerve to ischemic injury.

23. The method according to claim 22, further comprising the steps of estimating a pressure applied to the nerve over time and predicting a damage to the nerve based on the estimate of pressure applied to the nerve over time and a modeled sensitivity of the nerve to mechanical injury.

24. The method according to claim 22, wherein said optical sensor senses capillary blood in skin.

25. The method according to claim 22, wherein said optical sensor senses retinal blood flow.

26. The method according to claim 22, wherein the nerve is in the retina.

27. A sensor for predicting retinal damage due to externally applied forces, comprising a fluid filled bulb adapted for placement over the eyelid, covering the orbit and a tube for transmitting a pressure of the fluid to a pressure transducer.

28. The sensor according to claim 23, further comprising a pressure transducer for measuring a pressure of the fluid and an analyzer for determining risk of damage to the retina based on applied forces over time.

29. A method for predicting ischemic nerve damage due to external mechanical effects, comprising the steps of:
   (a) providing a transducer at a location of a patient to sense a mechanical effect which correlates with a local pressure to which a nerve is subjected;
   (b) measuring the mechanical effect over time by means of the transducer; and
   (c) predicting a damage to the nerve based on a susceptibility of the nerve to ischemic damage, a measured blood pressure of the patient and the measured mechanical effect over a period of time.

30. The method according to claim 29, further comprising the step of selectively producing an output if one or more conditions selected from the following group is met:
   (i) the measured mechanical effect correlates with an applied pressure which is in excess of diastolic pressure for a predetermined period;
   (ii) the measured mechanical effect correlates with an average applied pressure over an interval of time is in excess of a predetermined threshold;
   (iii) the measured mechanical effect correlates with an average applied pressure over an interval of time is in excess of a threshold dependent on the diastolic pressure; and
   (iv) the measured mechanical effect correlates with an applied pressure which, over the course of an interval of time is in excess of a predetermined threshold for a predetermined cumulative duration.

31. The method according to claim 29, further comprising the step of selectively producing an output if the measured mechanical effect correlates with an applied pressure which is in excess of diastolic pressure for a predetermined period.

32. The method according to claim 29, further comprising the step of selectively producing an output if the measured mechanical effect correlates with an average applied pressure over an interval of time is in excess of a predetermined threshold.

33. The method according to claim 29, further comprising the step of selectively producing an output if the measured mechanical effect correlates with an average applied pressure over an interval of time is in excess of a threshold dependent on the diastolic pressure.

34. The method according to claim 29, further comprising the step of selectively producing an output if the measured mechanical effect correlates with an applied pressure which, over the course of an interval of time is in excess of a predetermined threshold for a predetermined cumulative duration.

35. A method for predicting nerve damage due to external mechanical effects, comprising the steps of:

(a) placing a transducer external to a patient to measure a surrogate factor, relating to a local pressure is applied to a nerve as a result of a mechanical effect;

(b) measuring the surrogate factor;

(c) predicting a damage to the nerve based on the measured surrogate factor over time, and a model of susceptibility of the nerve to damage.

36. The method according to claim 35, wherein the surrogate factor is nerve conduction and the transducer measures a nerve conduction phenomena through the region of applied local pressure.

\* \* \* \* \*